United States Patent
Knepper

(10) Patent No.: US 11,698,064 B2
(45) Date of Patent: Jul. 11, 2023

(54) SYSTEM AND METHOD FOR OPERATING A PUMP IN A HUMIDIFIER

(71) Applicant: KONINKLIJKE PHILIPS N.V., Eindhoven (NL)

(72) Inventor: Michael B. Knepper, Friedens, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 592 days.

(21) Appl. No.: 16/219,022

(22) Filed: Dec. 13, 2018

(65) Prior Publication Data
US 2019/0201654 A1 Jul. 4, 2019

Related U.S. Application Data

(60) Provisional application No. 62/611,560, filed on Dec. 29, 2017.

(51) Int. Cl.
*F04B 43/04* (2006.01)
*F04B 49/06* (2006.01)
(Continued)

(52) U.S. Cl.
CPC ........... *F04B 43/04* (2013.01); *A61M 11/042* (2014.02); *A61M 16/0003* (2014.02);
(Continued)

(58) Field of Classification Search
CPC ...... F04B 43/04; F04B 43/0081; F04B 49/06; F04B 43/02; F04B 45/047; A61M 16/16;
(Continued)

(56) References Cited

U.S. PATENT DOCUMENTS 4,556,371 A * 12/1985 Post .................... F04B 11/0066
417/539
4,668,854 A * 5/1987 Swan ....................... F22B 1/287
392/399
(Continued)

FOREIGN PATENT DOCUMENTS

WO 2016067742 A1 5/2016

OTHER PUBLICATIONS

Horstkoffe, B. et al., "improving pressure robustness, reliability, and versatility of solenoid-pump flow systems using a miniature economic control unit including two simple pressure pulse mathematical models" Analytical Chemistry 2010, vol. 82, Nr: 16, pp. 6983-6990.
(Continued)

*Primary Examiner* — Nathan C Zollinger
*Assistant Examiner* — Geoffrey S Lee

(57) ABSTRACT

A pump arrangement for powering a pump in providing a controlled volume of water to a drip nozzle in a drip-feed humidifier. The pump arrangement includes: a pump having a solenoid; a processing unit; and a power supply electrically connected to the solenoid via a switch which is controlled by the processing unit. The power supply is structured to supply power to the solenoid via the switch. The processing unit is programmed to modulate the power provided to the solenoid via the switch such that the power is supplied to the solenoid according to a power profile for each actuation of the solenoid. The power profile includes: an initial portion which increases at a first overall rate, an intermediate portion which increases at a second overall rate different than the first overall rate, and a final portion which decreases at a third overall rate.

17 Claims, 13 Drawing Sheets

(51) Int. Cl.
| | |
|---|---|
| A61M 16/16 | (2006.01) |
| F04B 43/02 | (2006.01) |
| F04D 25/08 | (2006.01) |
| A61M 16/10 | (2006.01) |
| F04B 45/047 | (2006.01) |
| A61M 11/04 | (2006.01) |
| A61M 16/00 | (2006.01) |
| F04D 29/70 | (2006.01) |
| F04B 43/00 | (2006.01) |
| F04B 17/04 | (2006.01) |
| A61M 16/06 | (2006.01) |

(52) U.S. Cl.
CPC .... *A61M 16/0057* (2013.01); *A61M 16/0069* (2014.02); *A61M 16/024* (2017.08); *A61M 16/109* (2014.02); *A61M 16/1075* (2013.01); *A61M 16/16* (2013.01); *A61M 16/161* (2014.02); *F04B 43/0081* (2013.01); *F04B 43/02* (2013.01); *F04B 45/047* (2013.01); *F04B 49/06* (2013.01); *F04D 25/08* (2013.01); *F04D 29/705* (2013.01); *A61M 16/06* (2013.01); *A61M 2016/0018* (2013.01); *A61M 2016/0027* (2013.01); *A61M 2205/18* (2013.01); *A61M 2205/21* (2013.01); *A61M 2205/3334* (2013.01); *A61M 2205/3368* (2013.01); *A61M 2205/3653* (2013.01); *A61M 2205/75* (2013.01); *A61M 2205/7581* (2013.01); *F04B 17/04* (2013.01)

(58) Field of Classification Search
CPC .............. A61M 16/109; A61M 11/042; A61M 16/0057; A61M 16/0003; A61M 16/0069; A61M 16/161; F04D 25/08; F04D 29/705
See application file for complete search history.

(56) References Cited

U.S. PATENT DOCUMENTS

| | | | | |
|---|---|---|---|---|
| 5,348,585 | A | * | 9/1994 | Weston .............. H05K 13/0469 118/410 |
| 6,024,071 | A | * | 2/2000 | Heimberg .............. F02D 41/20 123/490 |
| 6,758,657 | B1 | * | 7/2004 | McNaull ................. F04B 43/04 417/415 |
| 2006/0096596 | A1 | | 5/2006 | Graham et al. |
| 2013/0240570 | A1 | * | 9/2013 | Johansson ............. F04B 17/044 222/333 |
| 2016/0101257 | A1 | * | 4/2016 | Lee ..................... A61M 16/164 128/203.27 |
| 2019/0078565 | A1 | * | 3/2019 | Carman ................. F04B 49/20 |

OTHER PUBLICATIONS

Liu, Y. et al., "In situ monitoring of atmospheric nitrous acid based on multi-pumping flow system and liquid waveguide capillary cell". Journal of Environmental Sciences, 2016, vol. 43. pp. 273-284.
International Search Report for PCT/EP2018/086045 dated Dec. 20, 2018.
Wikipedia, "Drop (liquid)", https://en.wikipedia.org/wiki/Drop_(liquid), Accessed Dec. 12, 2018.
Stan, C. et al., "Independent Control of Drop Size and Velocity in Microfluidic Flow-Focusing Generators Using Variable Temperature and Flow Rate", 2009, Department of Chemistry and Chemical Biology, Harvard University.
Martin, G. et al., "Inkjet printing—the physics of manipulating liquid jets and drops", Journal of Physics: Conference Series, 2008.

* cited by examiner

SYSTEM AND METHOD FOR OPERATING A PUMP IN A HUMIDIFIER

CROSS-REFERENCE TO PRIOR APPLICATIONS

This application claims the benefit of U.S. Provisional Application No. 62/611,560, filed on 29 Dec. 2017. This application is hereby incorporated by reference herein.

BACKGROUND OF THE INVENTION

1. Field of the Invention

The present invention pertains humidifiers for use in airway pressure support systems for delivering a flow of a humidified gas to the airway of a patient and, more particularly to systems and method for operating pumps in such humidifiers.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Humidifiers are frequently provided between or integral with a PAP machine and the user interface in order to humidify the otherwise relatively-dry compressed air generated by the PAP machine. Typically, humidifiers can be categorized as heated or passover types.

Heated humidifiers have a built-in heater that raises the temperature of the air being carried between the CPAP machine and the mask. Breathing in cold air can be discomforting and cause a sore throat. Most machines on the market today use a heated humidifier, as they tend to provide comfortable breathing conditions.

Passover type humidifiers are named as such because the air literally "passes over" the water in the humidifier on its journey from the machine to the mask. It wicks the moisture and similar to a heated humidifier, makes the air easier to breath and less irritating to the throat.

SUMMARY OF THE INVENTION

Accordingly, it is an object of the present invention to provide an improved humidifier and airway pressure support system including the same.

As one aspect of the disclosed concept, a pump arrangement for powering a pump in providing a controlled volume of water to a drip nozzle in a drip-feed humidifier. The pump arrangement comprises: a pump having a solenoid; a processing unit; and a power supply electrically connected to the solenoid via a switch which is controlled by the processing unit, the power supply is structured to supply power to the solenoid via the switch, wherein the processing unit is programmed to modulate the power provided to the solenoid via the switch such that the power is supplied to the solenoid according to a power profile for each actuation of the solenoid, and wherein the power profile comprises: an initial portion which increases at a first overall rate, an intermediate portion which increases at a second overall rate different than the first overall rate, and a final portion which decreases at a third overall rate.

The second overall rate may be greater than the first overall rate.

The second overall rate may be generally twice the first overall rate.

The initial portion may extend over about 20% of both an overall range and an overall time of the power profile from an initial positioning of an armature of the solenoid to a second positioning.

The initial portion may generally increase at a slow rate near the initial positioning which then increases near the second positioning.

The intermediate portion may extend over about 40% of the overall range and about 20% of the overall time from the second positioning to a third positioning.

The intermediate portion may generally increase at a greater rate closer to the second positioning and at a generally slightly slower rate closer to the third positioning.

The final may portion extend over about 40% of the overall range and about 60% of the overall time generally from the third positioning to a final positioning.

The final portion may decrease at generally a first rate near the third positioning and then at a decreasing rate nearing the final positioning.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
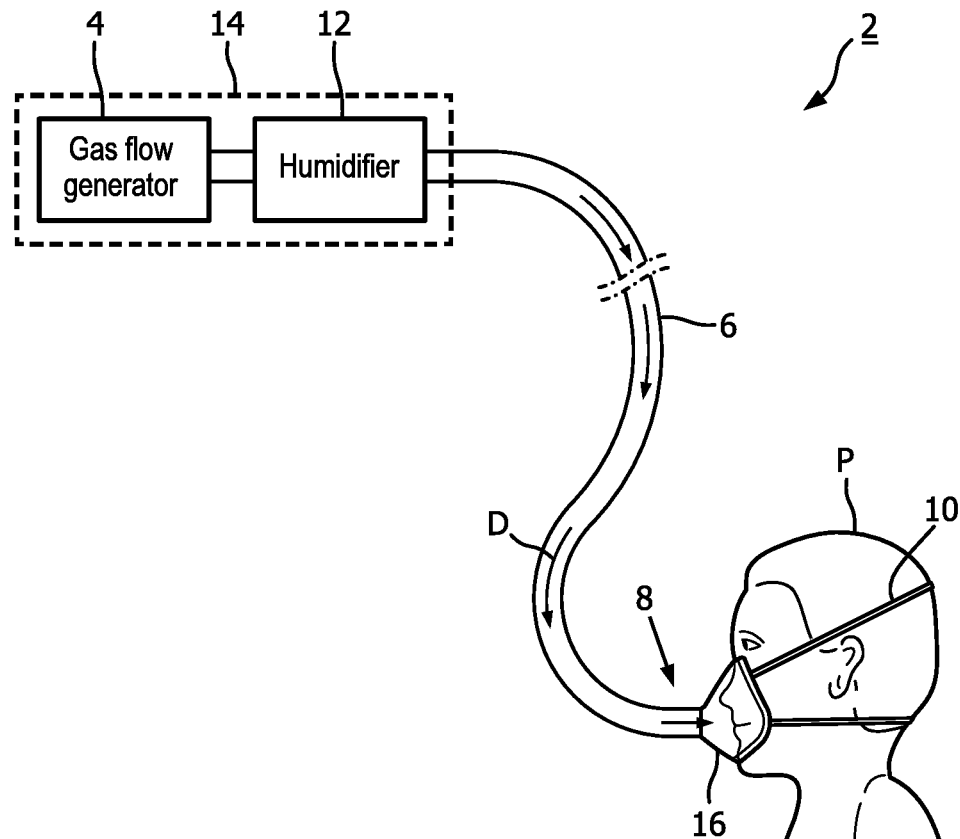
FIG. 1 is a schematic diagram of an airway pressure support system according to one particular, non-limiting embodiment in which the present invention in its various embodiments may be implemented, shown with a patient interface device thereof disposed on the face of a patient.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of an airway pressure support system 2 according to one particular, non-limiting embodiment in which the present invention in its various embodiments may be implemented. Pressure support system 2 includes a gas flow generator 4, a delivery conduit 6, a patient interface device 8 structured to engage about an airway of the patient, and a headgear 10 for securing patient interface device 8 to the head of a patient (P). Gas flow generator 4 is structured to generate a flow of breathing gas to be delivered through patient interface device 8 to the airway of patient P. The flow of breathing gas may be heated and/or humidified by a humidifier 12 provided either in a common housing 14 with gas flow generator 4 (such as shown in dashed line in FIG. 1) or alternatively, as a separate unit from, and located external, to pressure generating device 4. As discussed in further detail below, humidifier 12 is a drip feed humidifier.

Gas flow generator 4 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from gas flow generator 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. The present invention contemplates that gas flow generator 4 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment, patient interface device 8 includes a patient sealing assembly 16, which in the illustrated embodiment is a full face mask. It is to be appreciated, however, that other types of patient sealing assemblies, such as, without limitation, a nasal/oral mask, a nasal cushion, or any other arrangements which facilitate the delivery of the flow of breathing gas to the airway of a patient may be substituted for patient sealing assembly 16 while remaining within the scope of the present invention. It is also to be appreciated that headgear 10 is provided solely for exemplary purposes and that any suitable headgear arrangement may be employed without varying from the scope of the present invention.

Figure 2:
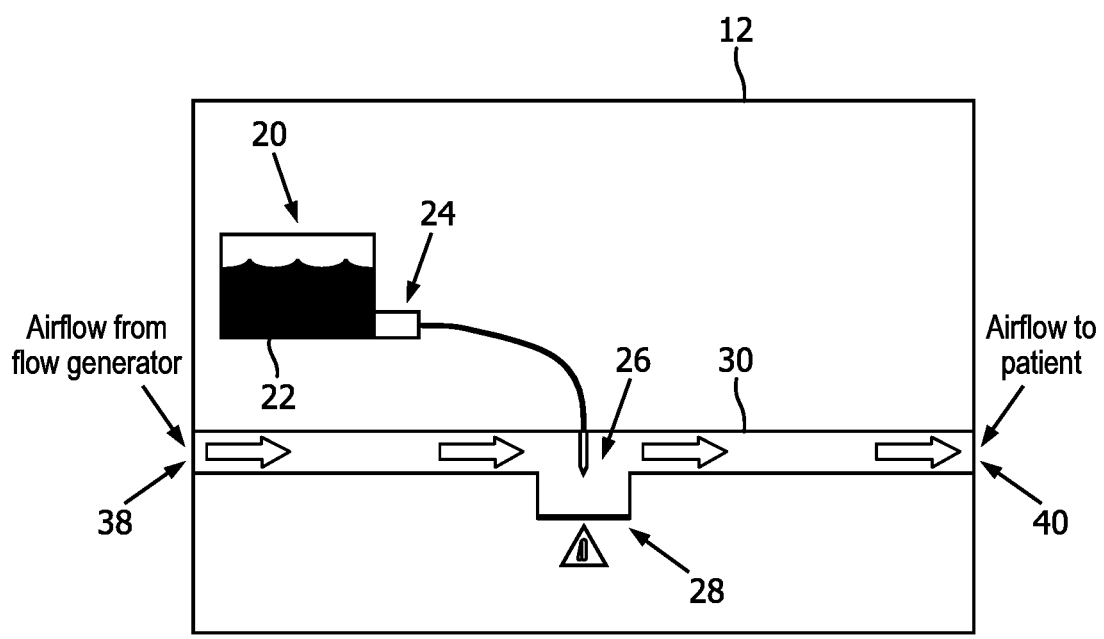
FIG. 2 is a schematic diagram of a humidifier according to one particular, non-limiting embodiment of the present invention in which various other example embodiments of the present invention may be implemented.

Referring to FIG. 2, drip feed humidifier 12 includes a water chamber 20 which is structured to house a suitable volume of water 22. Water is transferred at a predetermined rate from water chamber 20 by a solenoid-actuated pump (e.g., solenoid pump 24) or other suitable mechanism to a drip nozzle 26 which is disposed above a heater plate 28. Drip nozzle 26 and heater plate 28 are disposed within a conduit 30 which extends between a first end 38 (i.e., an inlet) and an opposite second end 40 (i.e., an outlet). First end 38 is structured to receive a flow of breathing gas, e.g., without limitation, from gas flow generator 4, which is then conducted by conduit 30 (as shown by block arrows) to second end 40 (and further to a patient). The amount of water 22 delivered to heater plate 28 is a function of the volume of solenoid pump 24 and the geometry of drip nozzle 26.

Figure 3:
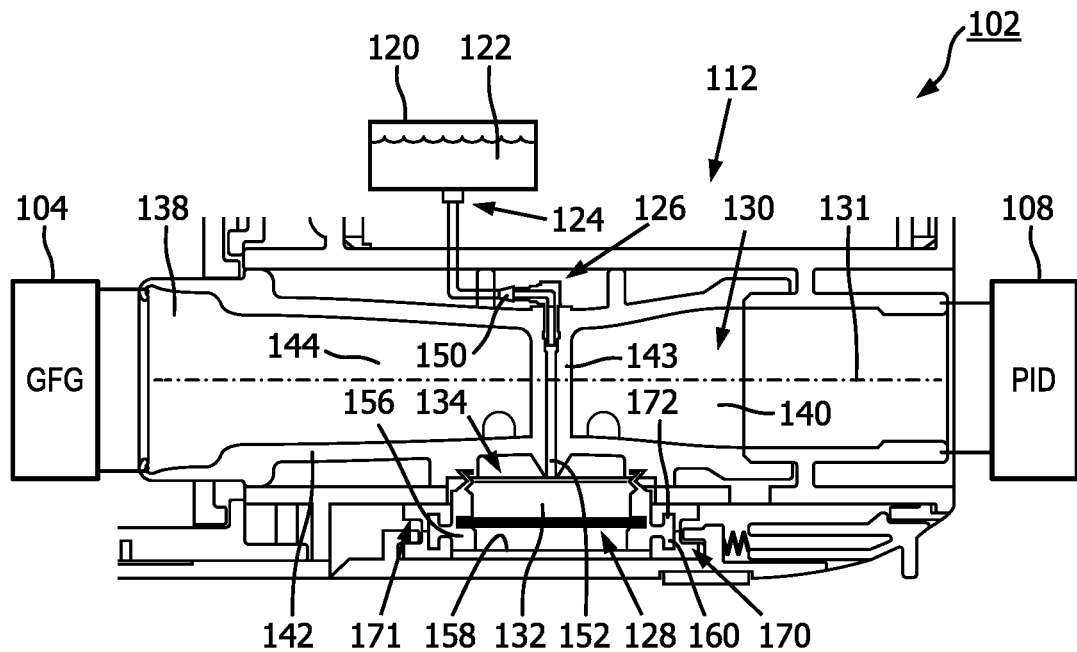
FIG. 3 is a partially schematic elevation sectional view of another airway pressure support system and humidifier for the same, according to one particular, non-limiting embodiment of the present invention taken along a plane lying on a longitudinal axis of the airflow pathway through the humidifier.

FIG. 3 is a partially schematic elevation sectional view of another airway pressure support system 102 including a humidifier 112 (see also FIG. 4) according to one particular, non-limiting embodiment of the present invention. Airway pressure support system 102 includes similar components, and functions similarly to, airway pressure support system 2, discussed above. As such, like numbers will be used to designate like components. Humidifier 112 includes a water chamber 120, a pump 124, a nozzle 126, a heater plate 128, a conduit 130, and a separator feature (e.g., without limitation, pocket 132). Conduit 130 includes a first end 138, an opposite second end 140, and a wall portion 142 defining an interior pathway 144 extending between first and second ends 138,140. First end 138 is fluidly connected to gas flow generator 104, and second end 140 is fluidly connected to patient interface device 108. Accordingly, it will be appreciated that interior pathway 144 of conduit 130 is structured to convey the flow of breathing gas generated by gas flow generator 104 between first end 138 and second end 140. Furthermore, wall portion 142 of conduit 130 includes a generally centrally disposed receiving portion 143 extending through interior pathway 144 and being located generally perpendicular to a longitudinal axis 131 of conduit 130. As shown, nozzle 126 extends at least partially through receiving portion 143.

Continuing to refer to FIG. 3, in one example embodiment humidifier 112 further includes a receiving member 134 and a number of frame members 170,171 each coupled to wall portion 142 of conduit 130. Receiving member 134 and frame members 170,171 cooperate to couple heater plate 128 to conduit 130. Pocket 132 is defined by receiving member 134. The function of pocket 132 will be discussed below, once the configuration of receiving member 134 and frame members 170,171, and the flow path of water 122, has been discussed.

Receiving member 134 may include an annular-shaped body portion 156 and a tongue member 160 extending radially outwardly from body portion 156. Furthermore, body portion 156 has an interior facing grooved region 158. As shown in FIG. 3, an outer periphery of heater plate 128 is located in and engaged with grooved region 158. Receiving member 134 may be made of any material structured to maintain the positioning of heater plate 128 without being structurally compromised (e.g., without limitation, silicone). Frame members 170,171, which in an example embodiment are made of a rigid thermoplastic material, may be coupled by any suitable mechanism known in the art (e.g., without limitation, being coupled by a snap-fit mechanism, being welded together), and preferably form a grooved region 172. Although the disclosed concept is being described in association with two frame members 170,171, it will be appreciated that a similar suitable alternative humidifier may include one frame member to couple to a receiving member, without departing from the scope of the disclosed concept. As shown, tongue member 160 of receiving member 134 is located in grooved region 172 in order to couple receiving member 134 to frame members 170,171 by a tongue and groove mechanism. It will, however, be appreciated that suitable alternative coupling mechanisms are contemplated by the disclosed concept.

Nozzle 126 is fluidly connected to water chamber 120 and is configured to produce a water droplet from water 122 received from water chamber 120. More specifically, nozzle 126 has an inlet 150 fluidly connected to water chamber 120 and an opposite outlet 152 from which the water droplet exists nozzle 126. Heater plate 128, which is coupled to wall portion 142, is positioned to receive the water droplet from nozzle 126. In one example embodiment, heater plate 128 is positioned directly below outlet 152, when viewed from the perspective of FIGS. 3 and 4. Furthermore, heater plate 128 is exposed to interior pathway 144. As such, in operation, when the water droplet exits outlet 152 and strikes heater plate 128, heater plate 128 is configured to cause the water droplet to evaporate and thus humidify the flow of breathing gas flowing from first end 138 of conduit 130 to second end 140 of conduit 130.

Figure 4:
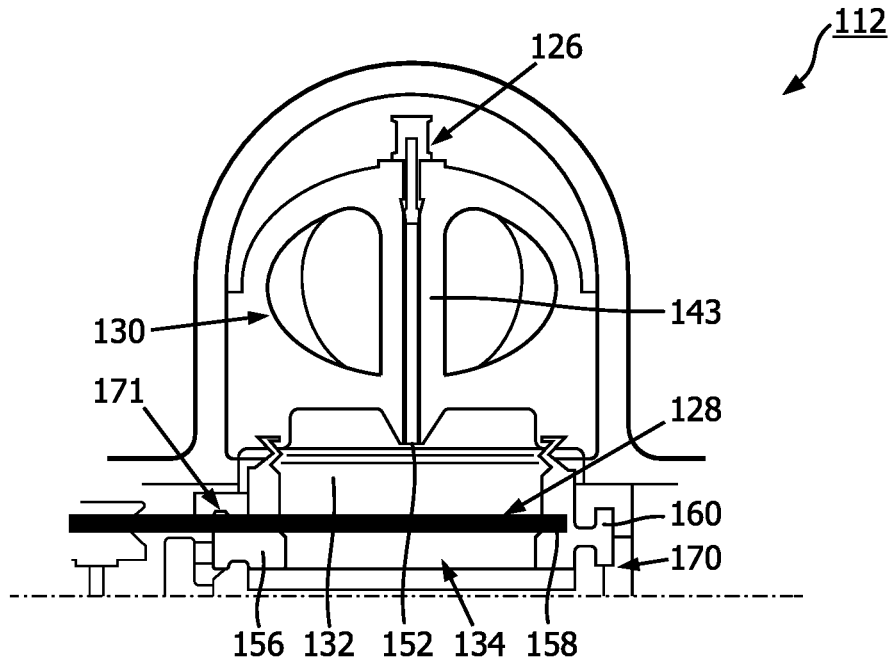
FIG. 4 is an elevation sectional view of the humidifier of FIG. 3, taken along a plane perpendicular to a longitudinal axis of the airflow pathway through the humidifier.

The function of pocket 132 will now be discussed in detail in conjunction with FIGS. 3 and 4. As shown, pocket 132, which is coupled to wall portion 142, extends away from interior pathway 144. In this manner, pocket 132 is configured to shield water droplets passing from outlet 152 of nozzle 126 to heater plate 128 from the flow of breathing gas. This significantly minimizes the likelihood that water will be undesirably blown into patient interface device 108. For example, in the event that water undesirably accumulates on heater plate 128 (e.g., is not quickly evaporated off of and/or exits outlet 152 too quickly), by locating outlet 152 in pocket 132, and heater plate 128 below outlet 152, the water will generally be maintained below and out of the gas stream. As such, the gas flow will generally not be strong enough to force any accumulated water through second end 140 of conduit 130 and into patient interface device 108. Rather, accumulated water, if any, will generally be maintained on heater plate 128 and/or engaged with receiving member 134, which defines pocket 132. Additionally, in the event of an undesirable tilt condition, where airway pressure support system 102 is inadvertently tilted such that it does not rest flat on the surface it is located on, water exiting outlet 152 that does not immediately evaporate will generally be maintained in pocket 132.

Figure 5:
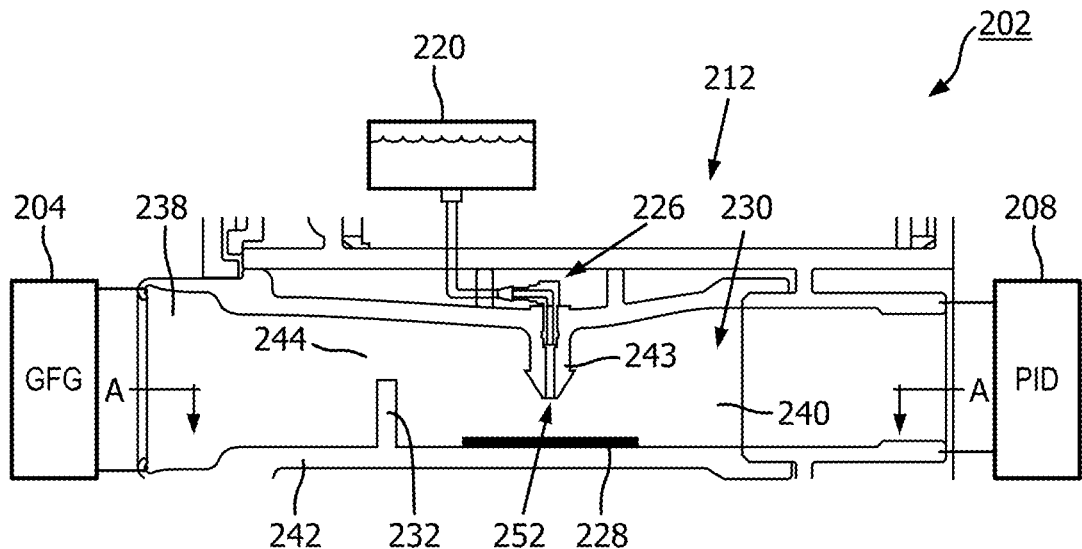
FIG. 5 is a partially schematic elevation sectional view of another airway pressure support system and humidifier for the same, according to one particular, non-limiting embodiment of the present invention taken along a plane lying on a longitudinal axis of the airflow pathway through the humidifier.

FIG. 5 is a partially schematic elevation sectional view of another airway pressure support system 202 including humidifier 212 (see also FIG. 6) according to one particular, non-limiting embodiment of the present invention. Airway pressure support system 202 includes similar components, and functions similarly to, airway pressure support systems 2 and 102, discussed above. As such, like numbers will be used to designate like components. Additionally, for ease of illustration and economy of disclosure, only significant distinctions will be discussed in detail.

Figure 6:
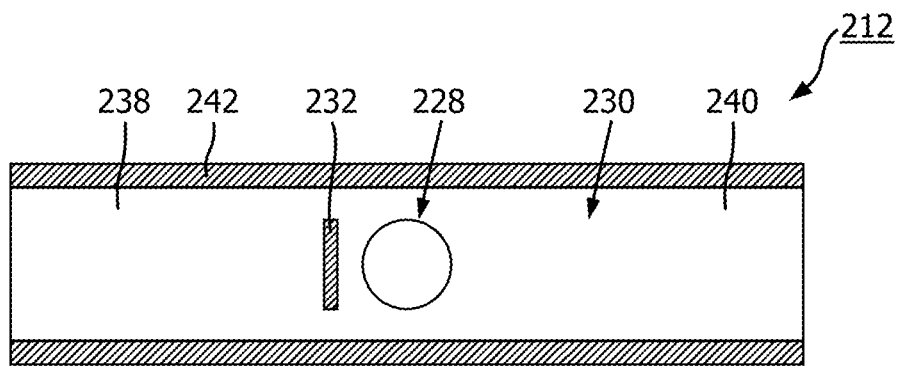
FIG. 6 is a simplified sectional view of a portion of the humidifier of FIG. 5, taken along line A-A of FIG. 5.

As shown in FIGS. 5 and 6, the separator feature of humidifier 212 is in the form of a wall portion (e.g., without limitation, generally planar member 232) extending radially inwardly from wall portion 242 of conduit 230. In one example embodiment, planar member 232 and wall portion 242 form a unitary component made from a single piece of material. As shown in FIGS. 5 and 6, planar member 232 is located between first end 238 and heater plate 228. As such, it will be appreciated that planar member 232 affords humidifier 212 substantially the same advantages as pocket 132 affords humidifier 112.

More specifically, in operation, planar member 232 minimizes the likelihood that accumulated water from water chamber 220 will be blown into patient interface device 208. Accordingly, planar member 232 advantageously safeguards against the possibility and/or ensures that the phase change of the water droplet from liquid to vapor will occur without a large likelihood of the water droplet being carried off through second end 240 by the velocity component of the breathing gas.

As shown in FIG. 5, humidifier 212 generally does not have a pocket. Heater plate 228 may be located at or above (i.e., from the perspective of FIG. 5) the elevation of wall portion 242. In the example of FIG. 5, heater plate 228 is generally located at a same elevation as wall portion 242 of conduit 230, and receiving portion 243 is shorter than receiving portion 143 of humidifier 112, such that it generally terminates in interior pathway 244. Accordingly, outlet 252 of nozzle 226 is generally located in interior pathway 244. Furthermore, planar member 232 functions as a barrier which obstructs gas flow from gas flow generator 204. That is, gas entering first end 238 from gas flow generator 204 will generally not have a direct path over heater plate 228, a situation which might otherwise result in accumulated water (e.g., water which might not have evaporated quickly enough and/or which might have accumulated as a result of exiting nozzle 226 too quickly) undesirably being blown through second end 240 and into patient interface device 208. However, heater plate 228 is still exposed to interior pathway 244, and as such, functions to evaporate water into interior pathway 244, thereby allowing humidified gas to exit second end 240 and be delivered to patient interface device 208.

Figure 7:
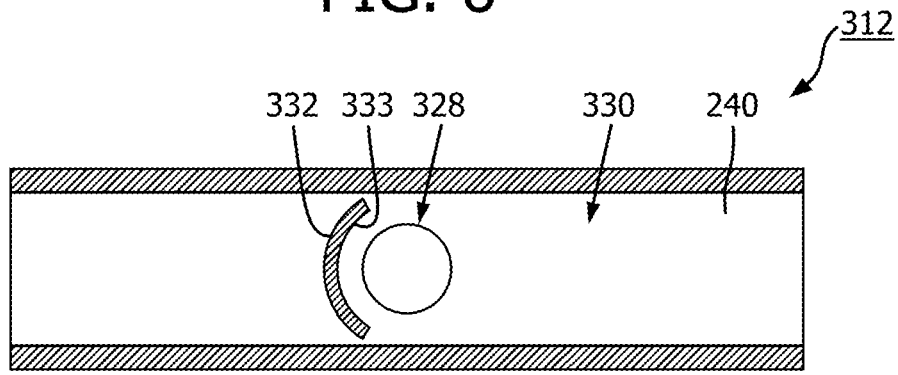
FIG. 7 is a simplified sectional view of a portion of another humidifier, according to one particular, non-limiting embodiment of the present invention.

FIG. 7 is a simplified sectional view of a portion of another humidifier 312, according to one particular, non-limiting embodiment of the present invention. Humidifier 312 is substantially the same as humidifier 212, discussed above. As such, like numbers will be used to designate like components. Additionally, for ease of illustration and economy of disclosure, only significant distinctions will be discussed in detail.

As shown in FIG. 7, wall portion 332 has a generally concave-shaped surface 333 facing heater plate 328. It will be appreciate that, while wall portion 332 provides substantially the same advantages to humidifier 312 as corresponding planar member 232 provides to humidifier 212, wall portion 332 provides additional advantages. Specifically, in operation, the concave geometry of wall portion 332 generally causes the flow of breathing gas to pass through conduit 330 with relatively little turbulence. That is, the flow of breathing gas will generally be prevented from flowing directly over heater plate 328, and will do so in a manner wherein it is smoothly deflected by wall portion 328.

It will be appreciated that humidifiers 112, 212, and 312 provide different examples of the disclosed concept. Specifically, each of humidifiers 112, 212, and 312 provides a unique mechanism by which water is protected from entering the gas stream and being blown into a corresponding patient interface device 108 and 208 (and the patient interface device of an airway pressure support system including humidifier 312). While the humidifiers 112, 212, and 312 each achieve this aim by virtue of separator features 132, 232, and 332, it will be appreciated that suitable alternative separator features that function to minimize and/or prevent water from entering the gas stream are contemplated herein.

Figure 8:
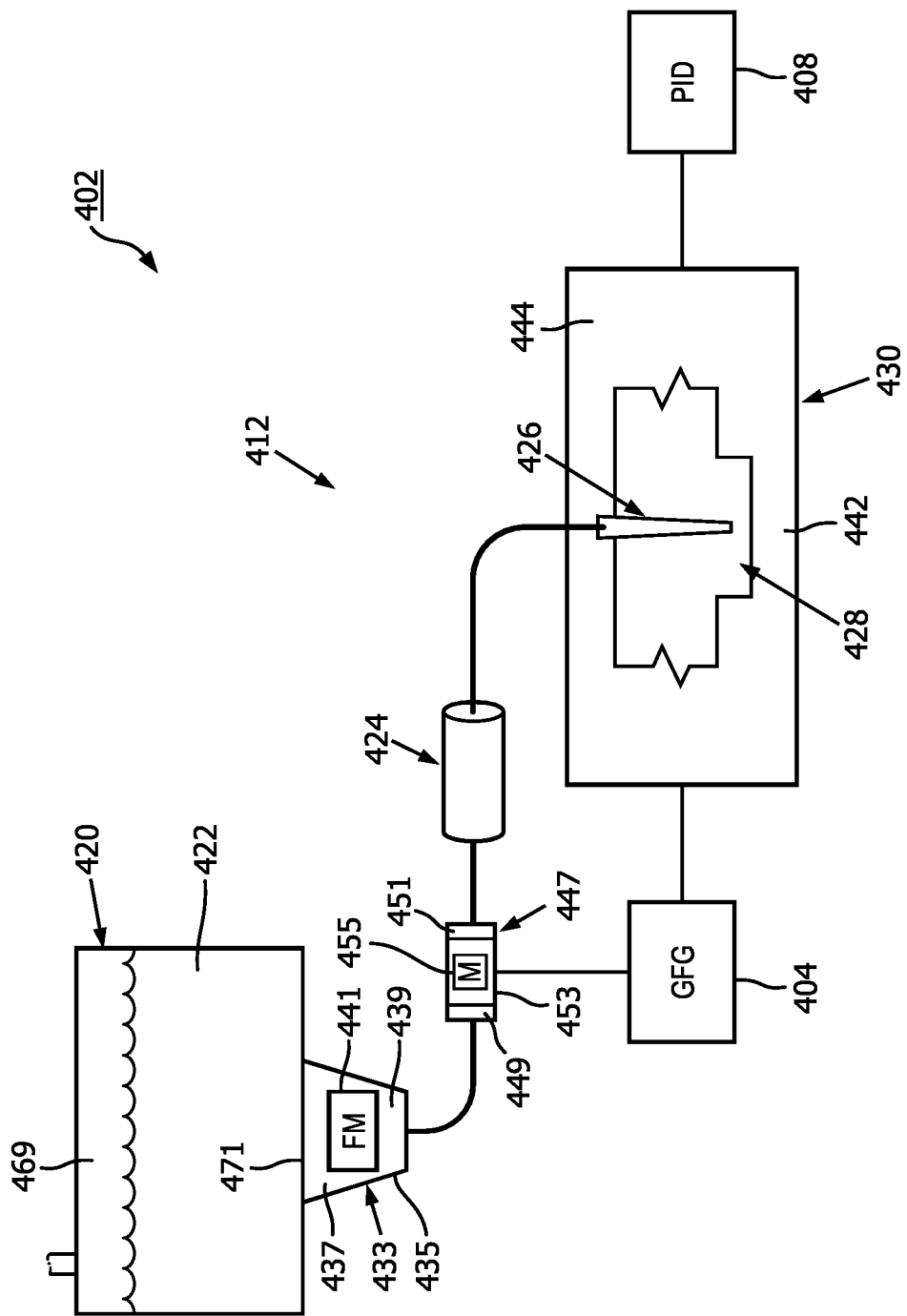
FIG. 8 is a schematic diagram of another airway pressure support system and humidifier for the same, according to one particular, non-limiting embodiment in which the present invention in its various embodiments may be implemented.
Figure 9:
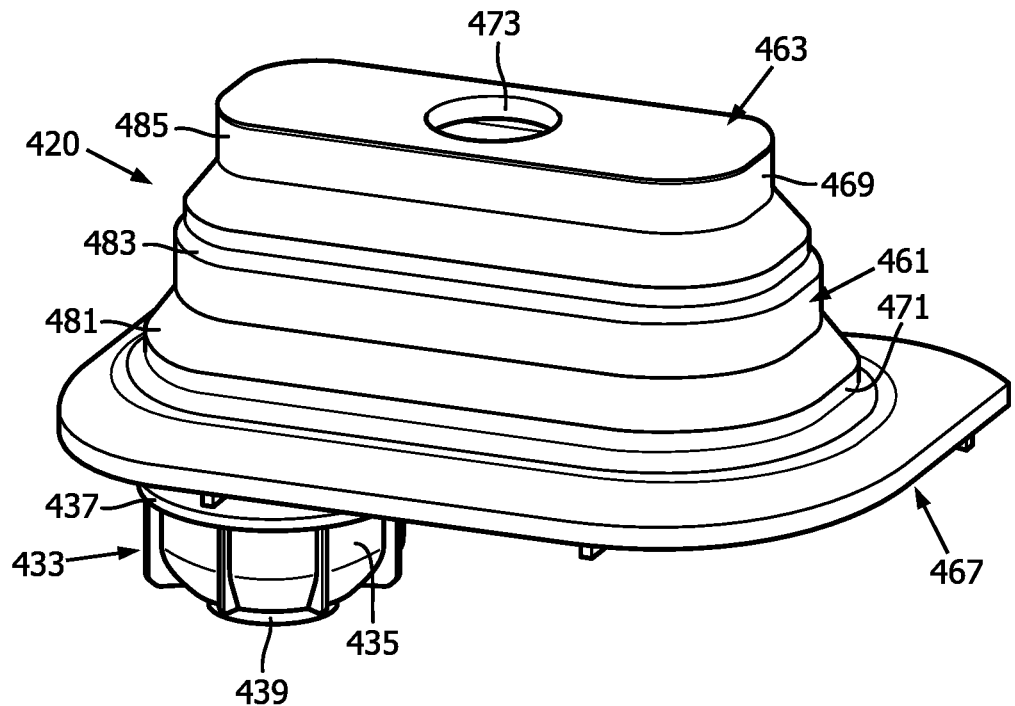
FIGS. 9 and 10 are isometric and front views, respectively, of a water chamber and filter for the airway pressure support system and humidifier for the same of FIG. 8, shown with the water chamber in a first position.
Figure 10:
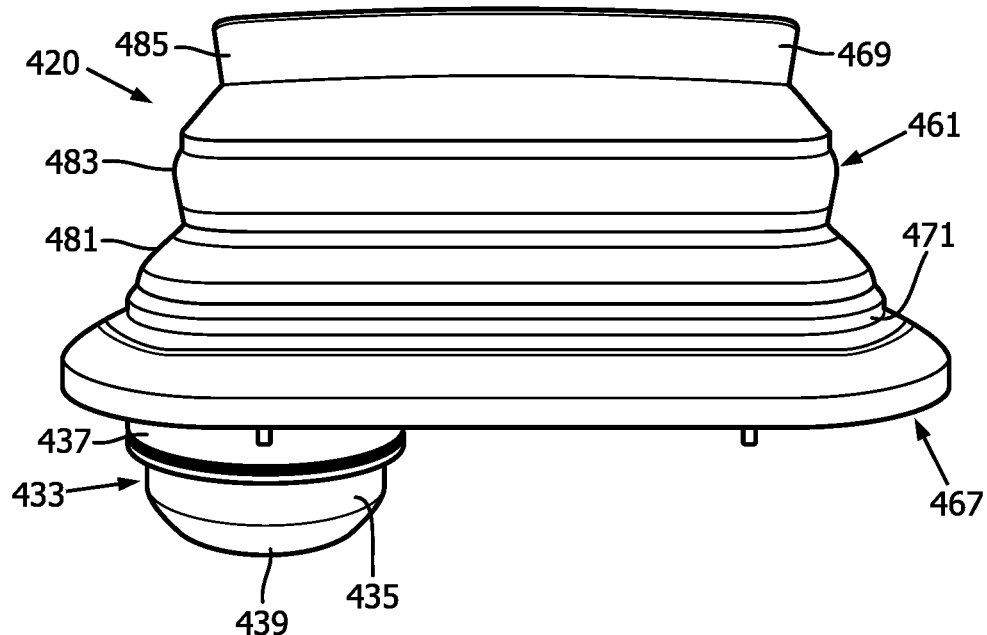

FIG. 8 is a schematic diagram of another airway pressure support system 402 including humidifier 412, according to one particular, non-limiting embodiment in which the present invention in its various embodiments may be implemented. Airway pressure support system 402 includes similar components, and functions similarly to, airway pressure support systems 2, 102, and 202 (and airway pressure support systems including humidifier 312), discussed above. As such, like numbers will be used to designate like components.

Gas flow generator 404 is configured to pass a flow of breathing gas through conduit 430 and further to patient interface device 408. Nozzle 426 is configured to produce a water droplet from water 422 received from water chamber 420. Heater plate 428, which is coupled to wall portion 442 of conduit 430, and is exposed to interior pathway 444, is positioned to receive the water droplet from nozzle 426. In this manner, when the water droplet evaporates and enters the gas flow stream, humidified breathing gas is able to be delivered to the patient through patient interface device 408.

In accordance with the disclosed concept, humidifier 412, and thus airway pressure support system 402, are further configured to minimize the likelihood that dissolved solids such as, for example and without limitation, calcium, magnesium, potassium, sodium, chlorides, sulfates, along with other organic matter, will be passed from water chamber 420 to pump 424, and/or left behind on heater plate 428 after the water droplets strike heater plate 428 and evaporate into interior pathway 444. For example, while humidifiers for airway pressure support systems are typically recommended to be used with distilled water, users will commonly use commercially available bottled or tap water (e.g., from a well or municipal water system) which may contain unwanted contaminants. While these alternate water types are not recommended for use, and generally do not have a detrimental effect on humidifier operation, they can be problematic for long-term usage of pumps, and generally leave behind the aforementioned contaminants as residue on heater plates. If the amount of residue becomes too great, components of humidifiers will generally have to be replaced. In order to address these concerns, humidifier 412 further includes a filter 433 and optionally a filtration meter 447.

Figure 11A:
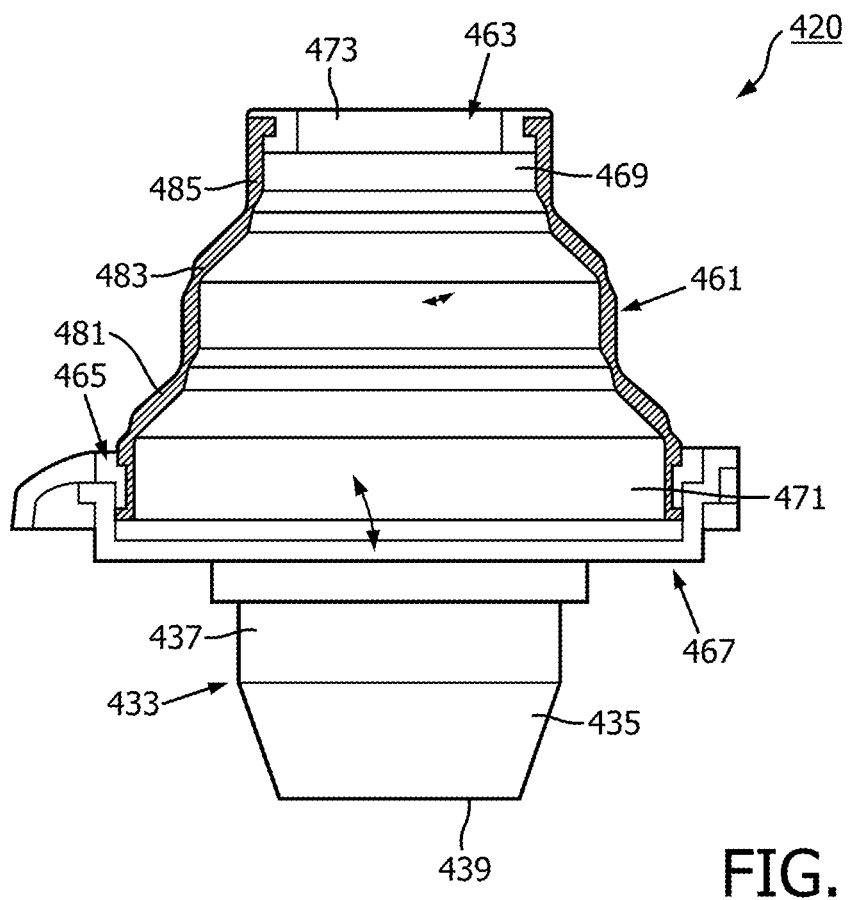
FIGS. 11A and 11B are sectional views of the water chamber and filter for the airway pressure support system and humidifier for the same of FIG. 8, shown with the water chamber in a first position and a second position, respectively.
Figure 11B:
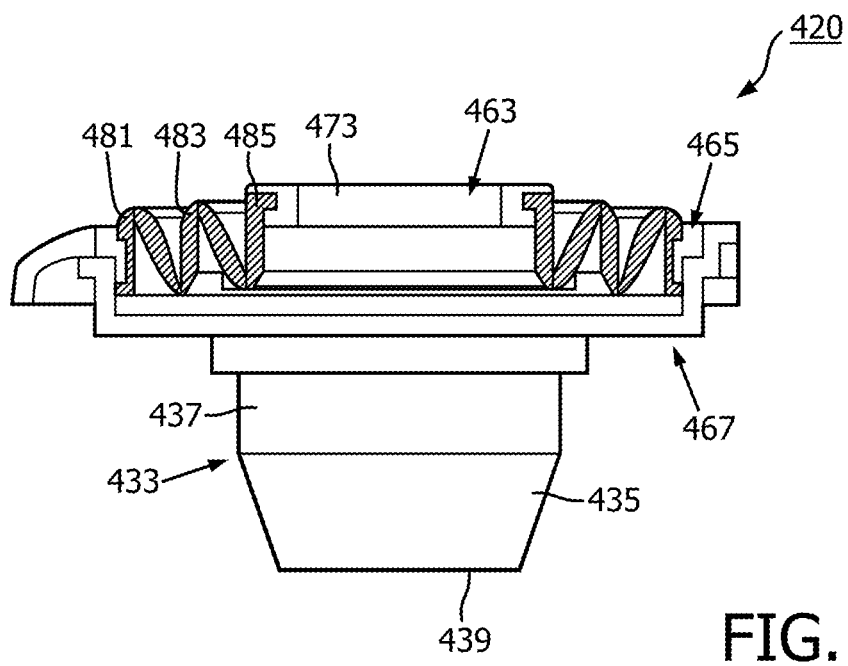
Figure 12:
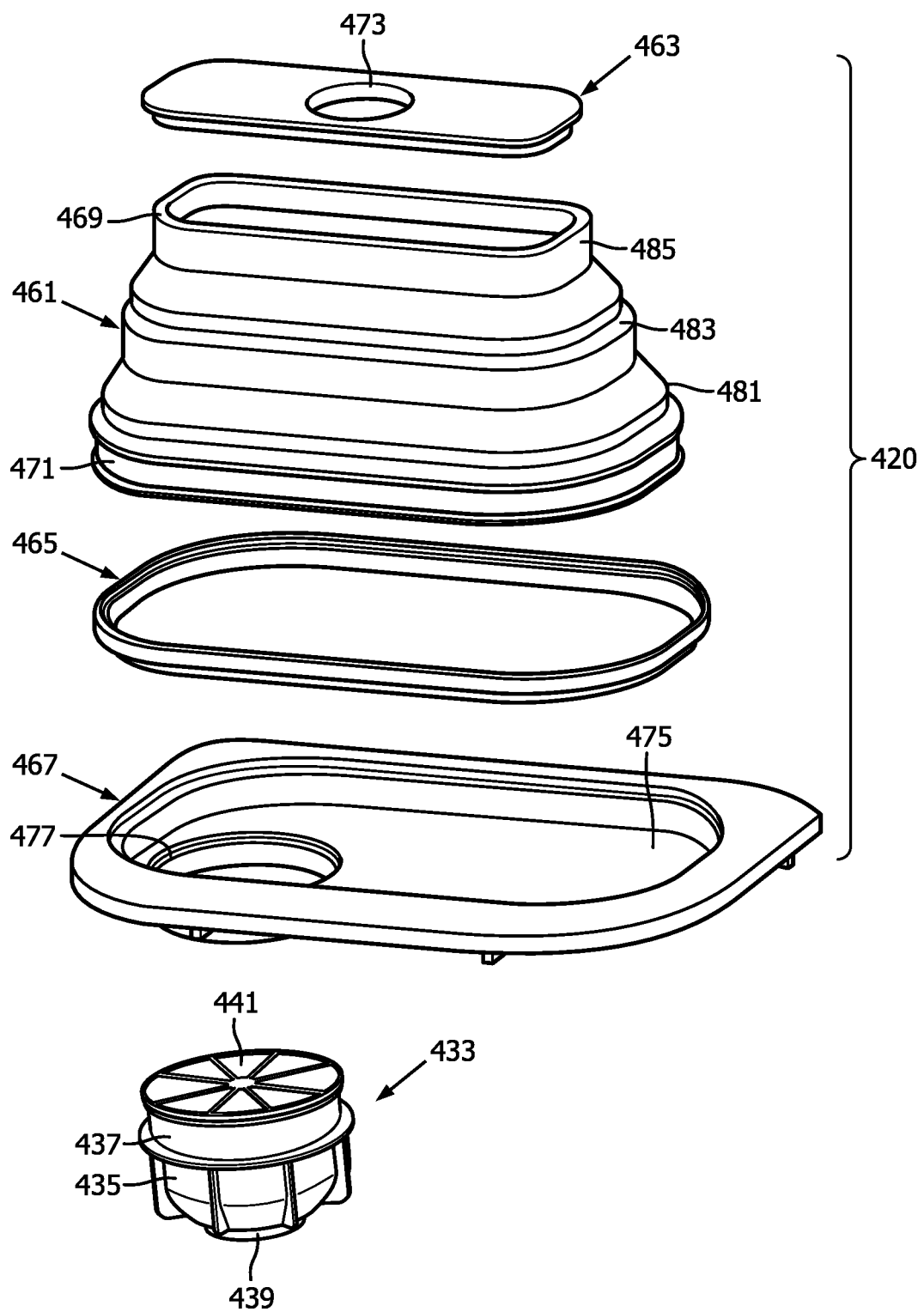
FIG. 12 is an exploded isometric view of the water chamber and filter of FIGS. 9-11.

FIGS. 9-14 show different views of water chamber 420 and filter 433. Referring to FIG. 12, water chamber 420 includes a flexible body portion 461, a cap 463, an annular-shaped retention member 465, and a base 467. Body portion 461 of water chamber 420 includes an inlet 469 and an opposite outlet 471. Cap 463 is selectively coupled to inlet 469, and has a vent passage 473 defined therethrough. As such, vent passage 473 is configured to allow air to enter water chamber 420 as the water level therein drops during use. Retention member 465 connects outlet 471 of body portion 461 to base 467. As shown in FIG. 12, base 467 has a body portion 475 that is selectively coupled to outlet 471 of body portion 461 of water chamber 420, and has a passage portion 477 defined therethrough.

Filter 433 has a housing 435 having an inlet 437 and an opposite outlet 439. Furthermore, housing 435 of filter 433 is structured to house a filtration medium 441 (partially shown in FIG. 12). In one example embodiment, inlet 437 of filter 433 is threadably connected to passage portion 477 of base 467, and fluidly connected with outlet 471 of body portion 461 of water chamber 420. As such, housing 435 of filter 433 may be directly coupled to water chamber 420. It will, however, be appreciated that suitable alternative coupling mechanisms are contemplated by the disclosed concept (e.g., without limitation, coupling via screws and/or bolts, snaps, and/or quarter turn features). Additionally, it is contemplated that a water chamber (not shown) may have any suitable alternative number of passages to allow water to drain from the water chamber into a filter. Furthermore, it is within the scope of the disclosed concept for a water chamber to be comprised of suitable alternative components and have a suitable alternative configuration.

Filtration medium 441 includes filter elements selected to remove the majority of dissolved solids from water 422 (FIG. 8) as it passes through filter 433, thus preparing it for boiling. The filter elements of filtration medium 441 may include one or more of a gross particle stainless steel mesh screen, activated carbon to remove chlorine and bacteria, ion exchange resin to remove many dissolved solids, a fiber mesh to contain the resin, and/or any other suitable components. It is also contemplated that outlet 439 of filter 433 may also contain a check valve to prevent water from flowing before the assembly of humidifier 412 is complete.

Figure 13:
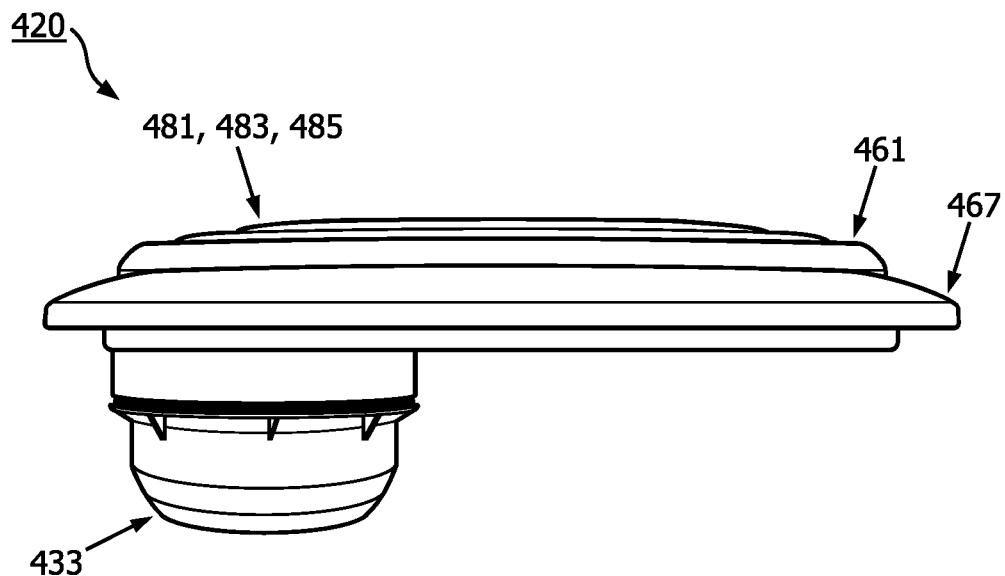
FIGS. 13 and 14 are front and isometric views, respectively, of the water chamber and filter of FIG. 12, shown with the water chamber collapsed to a second position.
Figure 14:
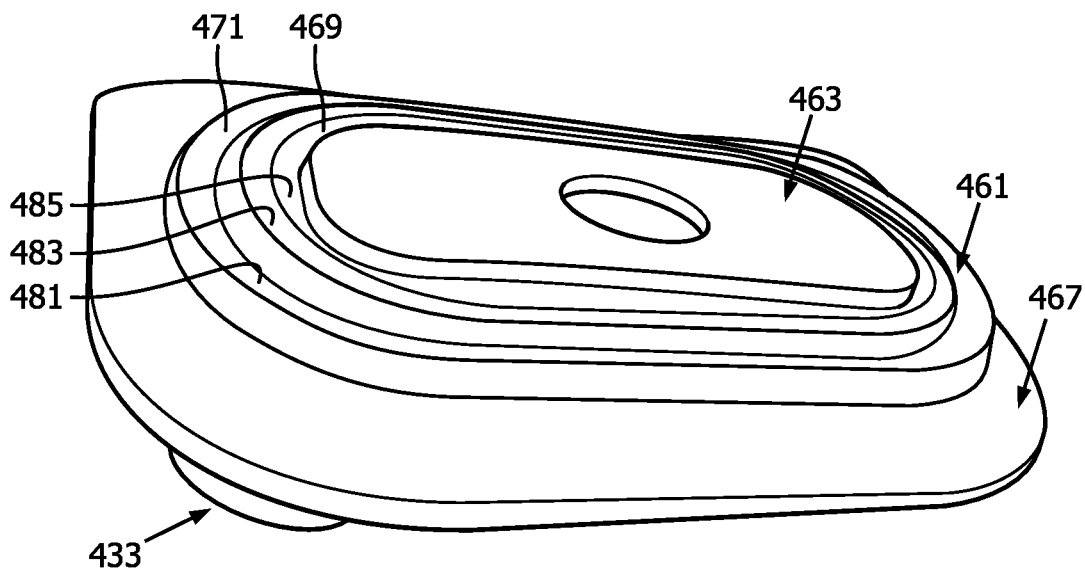

Water chamber 420 also provides improved advantages in terms of portability. More specifically, water chamber 420 is configured to collapse from a first (expanded) position, shown in FIGS. 9-11A, to a second (collapsed) position, shown in FIGS. 11B, 13 and 14. In order to function as such, body portion 461 of water chamber 420 is preferably made of a soft flexible material such as, for example and without limitation, silicone. When water chamber 420 is in the second position (FIGS. 11B, 13 and 14), inlet 469 is located internal and is generally concentric with respect to outlet 471. More specifically, body portion 461 has a plurality of ridge portions 481,483,485. Ridge portion 481 extends from outlet 471, ridge portion 485 extends from inlet 469, and ridge portion 483 extends between ridge portions 481,485. As shown most clearly in FIGS. 9-11A, when water chamber 420 is in the first position, ridge portions 481,483,485 are each in an extended position and are not concentric with respect to each other. As shown in FIGS. 11B, 13 and 14, when water chamber 420 is in the second position, ridge portions 481,483,485 are in a collapsed position such that they each are generally located at the same elevation (see FIGS. 11B and 13). As such, water chamber 420 is more easy to transport than existing water chambers because when not filled with water, it can relatively easily be configured so as to be less bulky and therefore easier to carry and store. In one example embodiment, when water chamber 420 is in the expanded position it protrudes outward from a housing of humidifier 412, and when water chamber 420 is in the collapsed position it is generally flush with a top surface of the housing of humidifier 412.

Referring again to FIG. 8, filtration meter 447 has an inlet 449, an outlet 451, a body portion 453 extending between inlet 449 and outlet 451, and a mechanism 455 located in body portion 453. Inlet 449 is fluidly connected to outlet 439 of filter 433. Body portion 453 of filtration meter 447 is structured to convey water from inlet 449 of filtration meter 447 to outlet 451 of filtration meter 447. One example configuration of humidifier 412 is provided wherein pump 424 is fluidly connected between outlet 471 of water chamber 420, and nozzle 426. In a preferred embodiment, pump 424 is fluidly connected between outlet 451 of filtration meter 447, and nozzle 426.

Mechanism 455 of filtration meter 447 is structured to measure filtration data of the water conveyed through body portion 453. In one example embodiment, mechanism 455 is electrically connected with a processing device (not numbered) of gas flow generator 404 in order to communicate the filtration data to gas flow generator 404. Accordingly, filter 433 and filtration meter 447 cooperate to provide humidifier 412 with a mechanism to remove dissolved solids from water 422 in the event that water 422 is not distilled.

More specifically, after water 422 has passed through filtration medium 441, and exits outlet 439 of filter 433, water 422 enters inlet 449 of filtration meter 447. In one example embodiment, filtration meter 447 is a total dissolved solids meter having two metal probes (e.g., without limitation, copper probes coated with a material, such as gold, to minimize corrosion). The probes may be the same size (e.g., without limitation, 1.5 millimeters in diameter with approximately 2 millimeters of length exposed to the water) and may be placed in parallel at approximately 5 millimeters center to center. As mechanism 455, which contains the probes, is electrically connected with gas flow generator 404, it will be appreciated that the board circuitry of gas flow generator 404 is configured to measure the electrical conductivity between the two probes. The electrical conductivity measurement may be converted to parts per million (hereinafter "PPM"), which provides an indication of the amount of dissolved solids contained in the water passing through filtration meter 447.

In a preferred embodiment, it is to be understood that water passing through filter 433 should have a dissolved solids content of less than 30 PPM. In the event that the dissolved solids measurement by filtration meter 447 is over 30 PPM, the electrical connection between filtration meter 447 and gas flow generator 404 will cause gas flow generator 404 to provide an indication (e.g., a screen reading) to a user that the water quality is too poor (e.g., contains too many dissolved solids), and that the filter needs to be changed. Furthermore, it is contemplated that humidifier 412 may not operate with a dissolved solids content over 30 PPM so as to protect pump 424 and heater plate 428. Furthermore, humidifier 412 is also configured such that once the dissolved solids content of the water reaches 20 PPM, the user will be notified on gas flow generator 404 that the filter is nearing the end of its life and should be replaced soon.

Once water 422 has passed through filtration meter 447, water 422 may flow into pump 424, which generates pressure to move water 422 to nozzle 426. As previously discussed, nozzle 426 is configured to generate the water droplet from water 422, and heater plate 428 is configured to receive the water droplet.

Accordingly, it will be appreciated that airway pressure support system 402 and humidifier 412 for the same are advantageously structured to function with any potable water (e.g., tap, bottled, distilled). Specifically, distilled water generally does not contain problematic dissolved solids, which might otherwise compromise components (e.g., pump 424 and heater plate 428) of humidifier 412. When tap and bottled water are used, while not advisable to users using humidifier 412, the water will advantageously be filtered by filtration medium 441 to remove many dissolved solids before exiting outlet 439. Furthermore, in addition to including filter 433, the failsafe of filtration meter 447 provides the additional advantage of alerting users of the quality of the water exiting outlet 439 of filter 433. That is, while filter 433 is generally configured to remove dissolved solids from the water, the extended use of filter 433 over time may compromise its ability to remove dissolved solids from the water. As such, filtration meter 447 provides a mechanism to address this concern. That is, mechanism 455, as discussed above, is readily configured to alert users of the quality of the water exiting outlet 439 of filter 433. If the quality is not appropriate (e.g., greater than 30 PPM), the user may receive an indication on gas flow generator 404 indicating that filtration medium 441 needs to be replaced. Once filtration medium 441 has been replaced by the user, non-distilled water, although not preferred, will once again be reliably filtered and passed to pump 424 and heater plate 428 with relatively little dissolved solids contained therein. As such, humidifier 412 is versatile in that it is readily configured to be employed with distilled water and non-distilled water without significant concern for compromising the integrity of operating components (e.g., pump 424 and heater plate 428).

Figure 15:
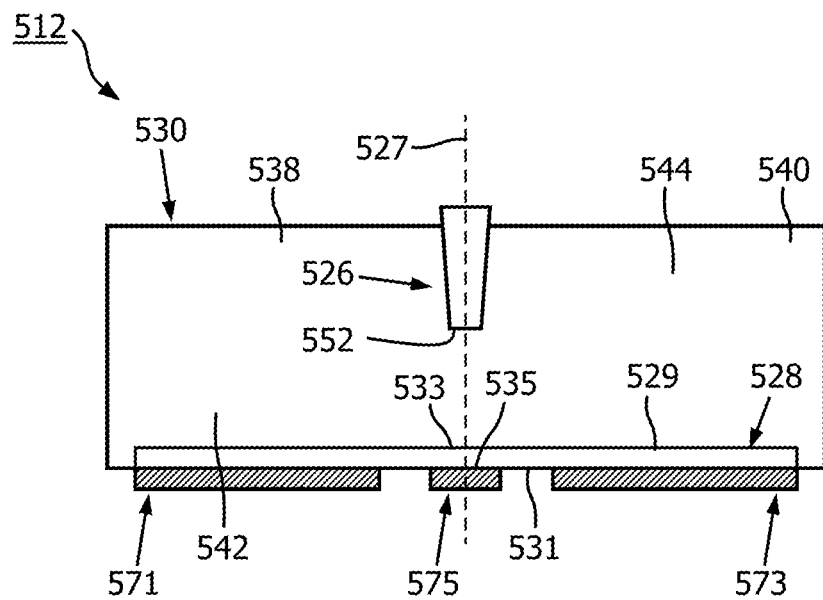
FIG. 15 is a schematic diagram of a portion of another humidifier for an airway pressure support system, according to one particular, non-limiting embodiment in which the present invention in its various embodiments may be implemented.

FIG. 15 is a schematic diagram of an enlarged portion of another humidifier 512 for an airway pressure support system, according to one particular, non-limiting embodiment of the present invention. Humidifier 512 includes similar components, and functions similarly to, humidifiers 12, 112, 212, 312, and 412, discussed above. As such, like numbers will be used to designate like components.

Conduit 530 includes a first end 538, a second end 540, a wall portion 542 defining an interior pathway 544 extending between first end 538 and second end 540. Nozzle 526 has an outlet 552 configured to produce a water droplet from water received from the water chamber (not shown). As shown, heater plate 528 has a first side 529 facing nozzle 526 and an opposite second side 531 facing away from nozzle 526. First side 529 is positioned to receive the water droplet from nozzle 526. In one example embodiment, humidifier 512 further includes a number of heating elements 571,573 coupled to second side 531 of heater plate 528. Heating elements 571,573 are configured to heat heater plate 528 in order to cause a water droplet striking first side 529 to evaporate, thereby humidifying the breathing gas.

Additionally, humidifier 512 may further include a thermistor 575 coupled to second side 531 of heater plate 528. Thermistor 575 may be located closer to outlet 552 of nozzle 526 than heating elements 571,573 are located to outlet 552 of nozzle 526. Thermistor 575 may be electrically connected (e.g., via a processing unit) to the gas flow generator of the airway pressure support system including humidifier 512, and allows the processing unit to monitor the temperature of heater plate 528. In this manner, thermistor 575 provides a mechanism to detect whether water droplets exiting outlet 552 are hitting heater plate 528.

Continuing to refer to FIG. 15, first and second sides 529,531 of heater plate 528 each have a corresponding central location 533,535 located closer to outlet 552 than any other corresponding location on first and second side 529, 531. Central location 533 may be located directly opposite central location 535. When viewed from a top plan view (e.g., see FIG. 16), central locations 533,535 are located directly below outlet 552. In one example embodiment, thermistor 575 is located at central location 535 of second side 531. As shown, nozzle 526 is generally located about a longitudinal axis 527 extending through first and second sides 529,531, and which does not pass through heating elements 571,573.

Figure 16:
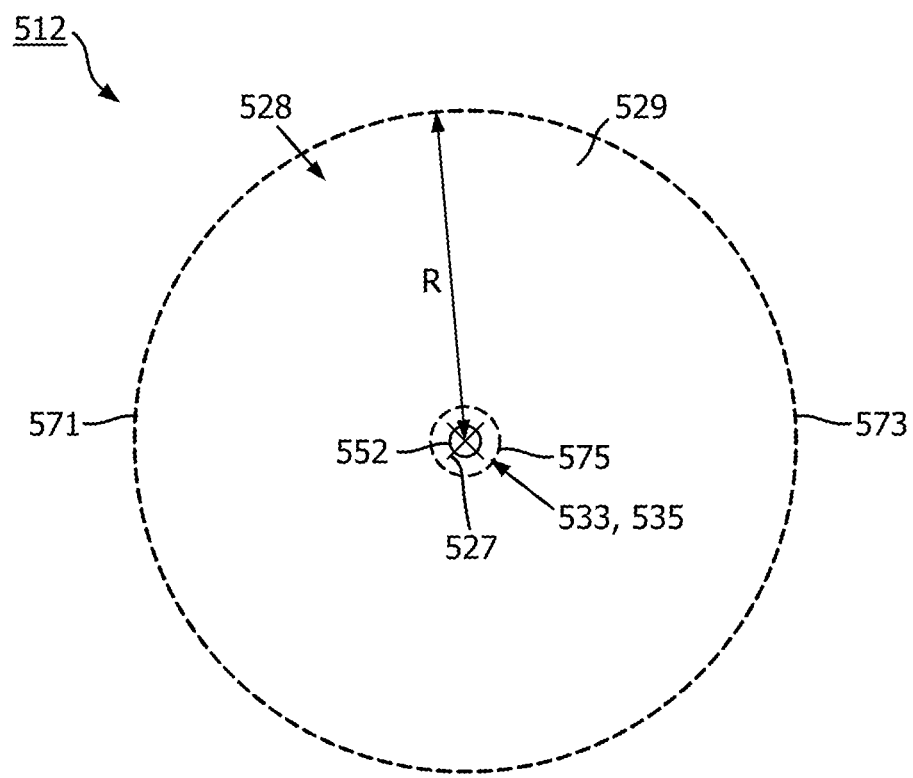
FIG. 16 is a simplified top plan view of a portion of the humidifier of FIG. 15.

It will thus be appreciated that heater plate 528 generally has a centrally located "no heat zone," depicted most clearly in FIG. 16 which is free from any heating elements. Specifically, the innermost boundary of heating elements 571, 573 is shown as the outer dashed circle, and the space internal thereto is the "no heat zone." As shown, heating elements 571,573 are spaced at least a radius R from central locations 533,535.

Figure 17:
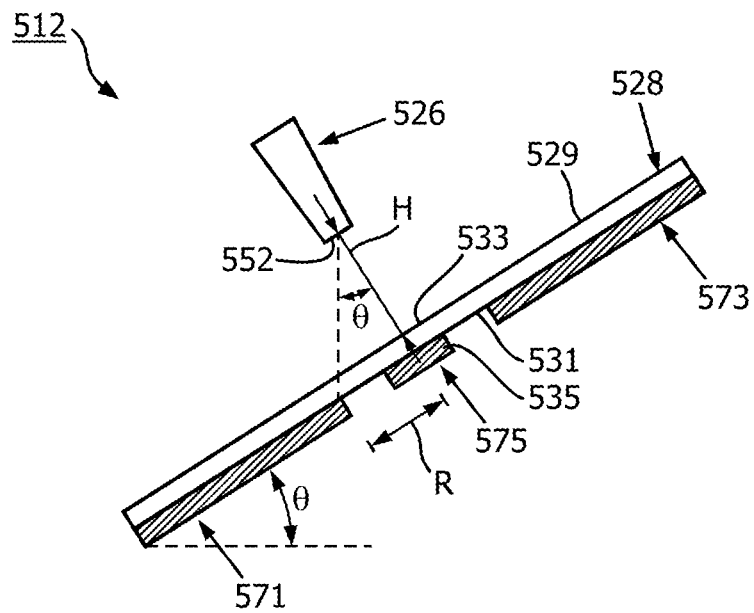
FIG. 17 is another schematic diagram of the portion of the humidifier of FIG. 15, shown with the humidifier rotated a maximum operating angle.

Referring to FIG. 17, a determination of the spacing of outlet 552 of nozzle 526 from heater plate 528 will now be discussed in detail. As shown, outlet 552 is located a height H above central location 533 of first side 529. The inventors have discovered that when H is less than about 4 millimeters, boiling water bubbles caused by the water droplets striking heater plate 428, will often bounce and strike outlet 552, a situation which can cause nozzle 426 to draw more water from the water chamber than may be desirable. As such, the inventors have discovered that H is preferably in the range of about 4 millimeters to about X millimeters, where X=(radius R)/tangent (θ).

In the example shown in FIG. 17, humidifier 512 has been tilted to a maximum operating angle θ. Angle θ may correspond to humidification standard ISO 8185:2007 or any other predetermined maximum sage operating angle. In one example embodiment, angle θ is about 20 degrees, and radius R is about 3 millimeters. In other words, thermistor 575 may be spaced at least 3 millimeters from each of heating elements 571,573. Accordingly, in one example embodiment H may be about 6 millimeters. At this elevation, water striking heater plate 528 will generally be far enough away from outlet 552 that it will not cause nozzle 526 to inadvertently draw more water from the water chamber than necessary. Furthermore, at this elevation, water droplets striking heater plate 528 will generally be close enough that in the event of an inadvertent or undesirable tilt condition (e.g., up to maximum operating angle θ), thermistor 575 will still be able to detect whether a water droplet has struck heater plate 528.

Figure 18:
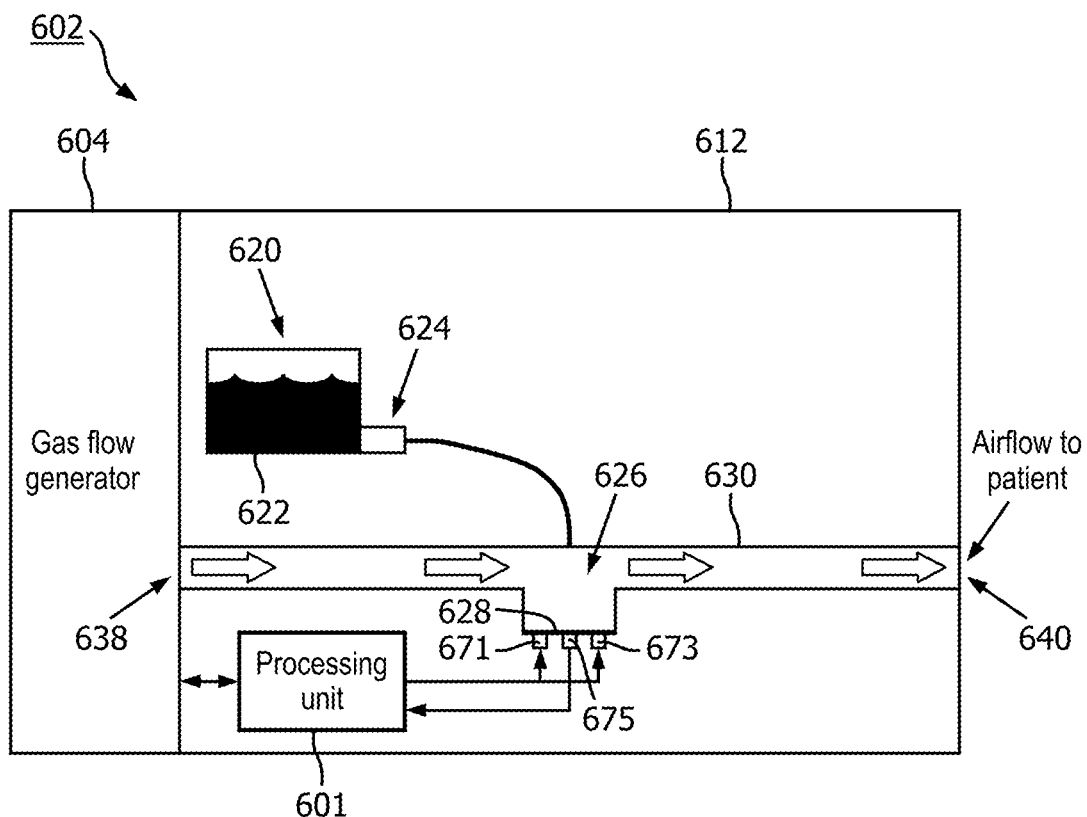
FIG. 18 is a schematic diagram of a gas flow generator and humidifier of an airway pressure support system according to one particular, non-limiting embodiment of the present invention.

FIG. 18 is a schematic diagram of gas flow generator 604 and humidifier 612 of an airway pressure support system 602 according to one particular, non-limiting embodiment of the present invention. Similar to the humidifier arrangements previously discussed, humidifier 612 includes a pump 624 for supplying a flow of water 622 from a water chamber 620 to a drip nozzle 626. Drip nozzle 626 is positioned to deliver water droplets to a heater plate 628 having a thermistor 675 and heating elements 671, 673 arranged as discussed in regard to the embodiment of FIGS. 15-17. Pressure support system 602 includes a processing unit 601 which may be a portion of humidifier 612 (as shown), a portion of gas flow generator 604, or as a separate element. Processing unit 601 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of gas flow generator 604, pump 624 and heating elements 671 and 673, as well as for receiving inputs from elements of gas flow generator 604 and from thermistor 675.

Figure 19:
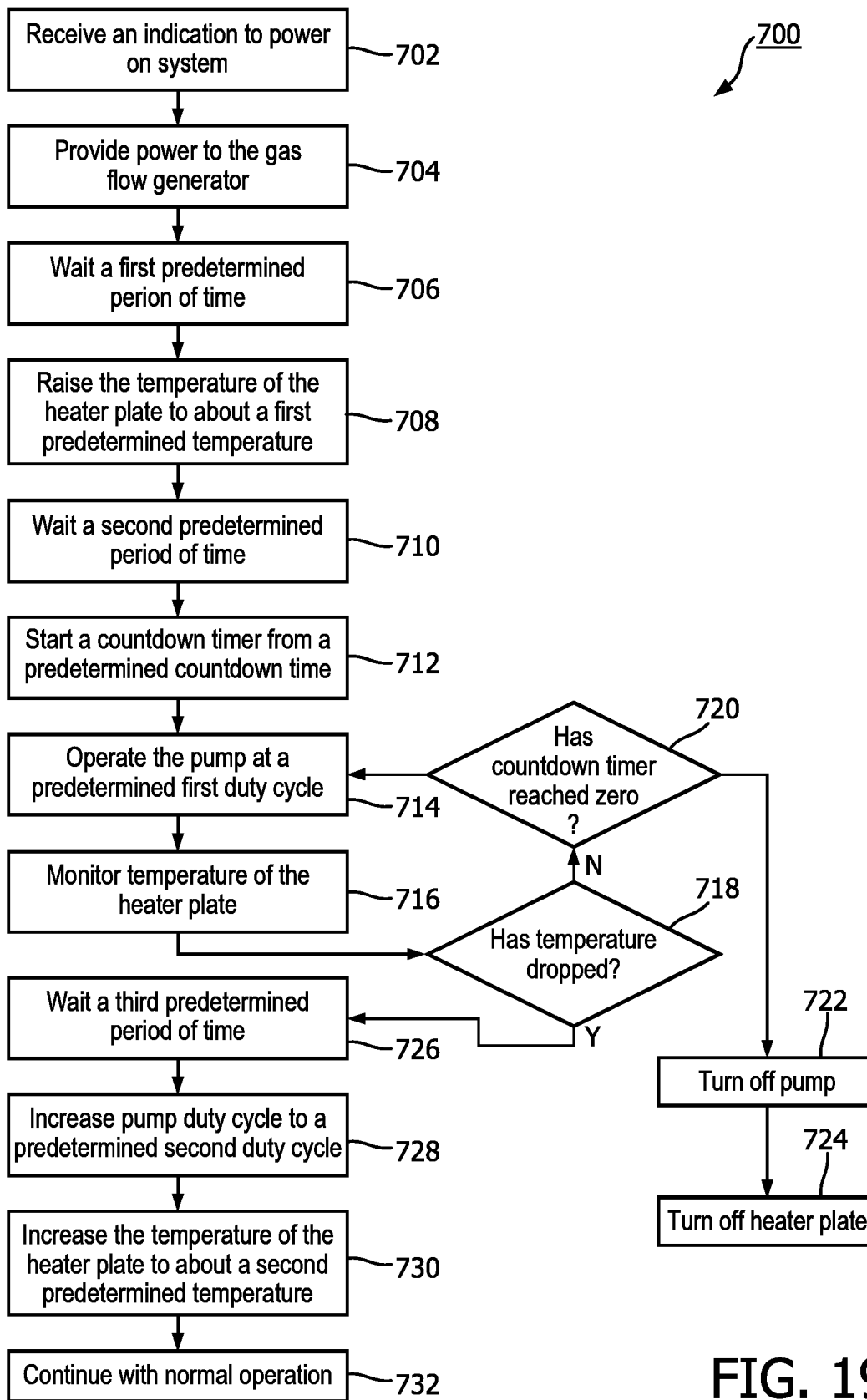
FIG. 19 is a flow chart of a method for starting a humidifier according to one particular, non-limiting embodiment of the present invention.

A flow chart of an example method 700, which may be carried out according to one particular, non-limiting embodiment of the present invention, which may be carried out by processing device 601 in starting humidifier 612 is shown in FIG. 19. Method 700 begins at 702 wherein an indication to power on system 602 is received. Typically such indication is received from an input device (not shown) such as a power button or other suitable arrangement which may be actuated by a patient, caregiver, or other person to initiate a pressure treatment session. Upon receiving the indication at 702, power is provided to gas flow generator 604, as shown at 704, such that a flow of air starts to pass through conduit 630 of humidifier 612 and onward to the patient. As shown at 706, such flow is allowed to continue for a first predetermined time which, in an example embodiment of the present invention, is 10 seconds, although other time increments may be employed without varying from the scope of the present invention.

Next, as shown at 708, the temperature of heater plate 628 is raised from generally the temperature of the ambient environment to a first predetermined temperature by a power supply provided to one or more of heating elements 671 and 673. In an example embodiment of the present invention, such first predetermined temperature is about 50° C., although other temperatures may be employed without varying from the scope of the present invention. As previously discussed in regard to the arrangement of FIGS. 15-17, the temperature of heater plate 628 is readily determined by monitoring the resistance of thermistor 675.

Once the temperature of heater plate 628 has reached the first predetermined temperature, the temperature is held at the first predetermined temperature for a second predetermined period of time, such as shown at 710. In an example embodiment of the present invention such second predetermined period of time is 10 seconds, although other time increments may be employed without varying from the scope of the present invention. Once the second predetermined period of time has elapsed, a countdown timer counting down from a predetermined countdown time is started, as shown at 712, and a sufficient power is supplied to pump 624 so as to begin operating pump 624 at a first predetermined duty cycle, such as shown at 714. In an example embodiment of the present invention, such first predetermined duty cycle is about a 20% duty cycle, although other suitable duty cycles may be employed without varying from the scope of the present invention. In an example embodiment of the present invention, the countdown timer is set for five minutes, although other time periods may be utilized without varying from the scope of the present invention.

Once pump 624 begins operating at 714, the temperature of heater plate 628 is monitored (via thermistor 675), as shown at 716. As shown in 718 and 720, such monitoring continues until either a drop in temperature is detected or until the countdown timer reaches zero. If the countdown timer reaches zero at 720 before a temperature drop is detected in 718, thus indicating that no water has struck heater plate 628 (due to lack of water in water chamber 620, failed pump, a blockage somewhere between water chamber 620 and nozzle 626, or some other problem) then pump 624 is turned off, as shown as 722, as well as heater elements 671 and 673, as shown at 724. Optionally, a signal or message may be provided to the patient via any suitable means to indicate that the humidifier has shut off. Alternatively, if a drop in temperature is detected at 718 before the countdown timer reaches zero, thus indicating that a water droplet or droplets have struck heater plate 628 (i.e., temperature of heater plate drops slightly due to vaporization of water droplets striking plate), the duty cycle of pump 624 is increased at 728 to a predetermined second duty cycle after waiting for a third predetermined period of time, such as shown at 726. In an example embodiment of the present invention, such second duty cycle is about a 25% duty cycle, although other suitable duty cycles may be employed without varying from the scope of the present invention. In an example embodiment of the present invention such third predetermined period of time is twenty seconds, although other suitable time increments may be employed without varying from the scope of the present invention.

After increasing the pump duty cycle at 728, the temperature of heater plate 628 is increased to about a second predetermined temperature (which coincides with a normal operating temperature) as shown at 730. In an example embodiment of the present invention, such second predetermined temperature is about 120° C., although other suitable temperatures may be employed without varying from the scope of the present invention. After reaching the second predetermined temperature, the humidifier continues on with normal operation. From the foregoing it is thus to be appreciated that method 700 provides a startup mechanism that keeps the heater plate from being fully powered until it is verified that water is being delivered to the heater plate. Additionally, by wetting the heater plate at a low temperature, any solids (from impurities in water provided in the water chamber) which have been previously deposited on the heater plate do not break up and release into the airstream. Hence, such method also reduces/eliminates the release of obnoxious gas which can otherwise be released from such solids.

Figure 20:
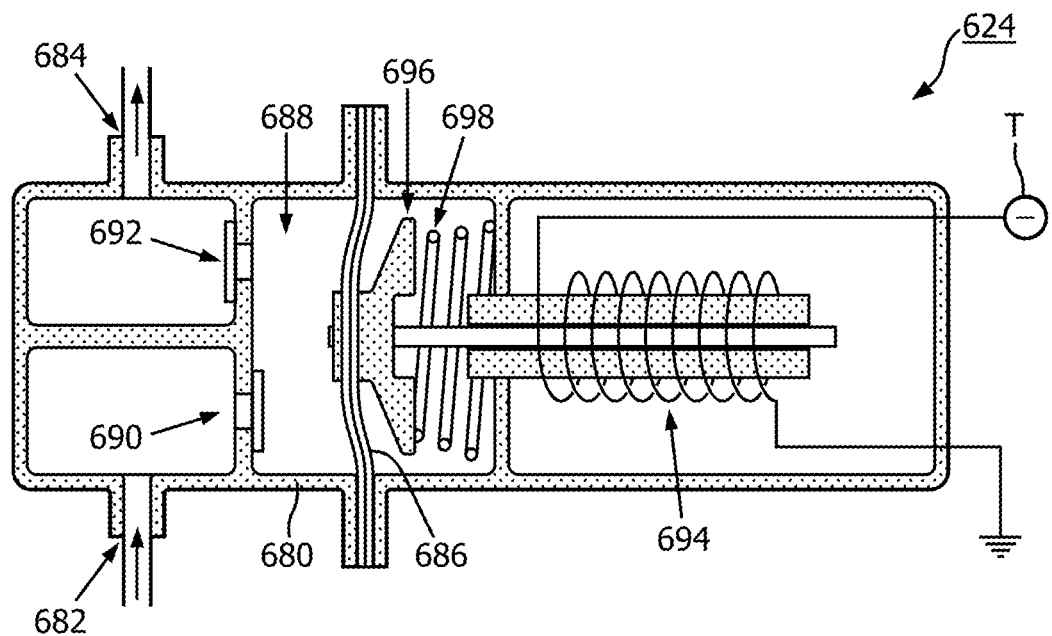
FIG. 20 is a schematic sectional view of an example pump according to one particular, non-limiting embodiment of the present invention.

FIG. 20 is a schematic sectional view of an example solenoid pump, such as pump 624 of FIG. 18 according to one particular, non-limiting embodiment of the present invention. Pump 624 includes a housing 680 having an inlet 682 and an outlet 684 defined therein. Pump 624 further includes a deformable diaphragm member 686 which, along with a portion of housing 680 defines a pumping chamber 688. Pumping chamber 688 is separated from inlet 682 via a one-way inlet valve 690, which only allows fluid to flow into pumping chamber 688, and from outlet 684 via a one-way delivery valve 692, which only allows fluid to flow out from pumping chamber 688. Pump 624 further includes a solenoid 694, which when energized by applying power to a terminal T, causes an armature 696 to deform diaphragm member 686 in a manner which reduces the volume of pumping chamber 688, and thus forces fluid from pumping chamber 688 via delivery valve 692 and out outlet 684. Pump 624 further includes a spring member 698 which is tensioned so as to pull armature 696 back toward solenoid 694, thus moving diaphragm member 686 back into an initial position and increasing the volume of pumping chamber 688. As the volume of pumping chamber 688 is increased, fluid is pulled into pumping chamber 688 via inlet 682 and inlet valve 690.

Figure 21:
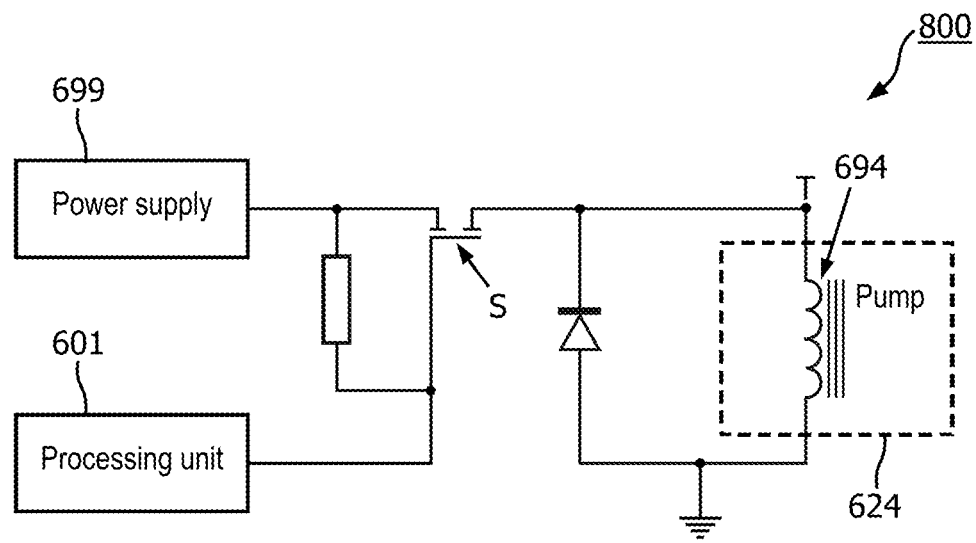
FIG. 21 is an example wiring schematic for a pump according to one particular, non-limiting embodiment of the present invention.

FIG. 21 is an example wiring schematic for an example pump arrangement 800 for powering a pump in a drip-feed humidifier, such as pump 624 of FIGS. 18 and 20, according to one particular, non-limiting embodiment of the present invention. Power to terminal T of solenoid 694 is selectively provided from a power supply 699 which is electrically connected to terminal T via a switch S. Switch S is controlled by a suitable microprocessor, such as processing unit 601, previously described in conjunction with FIG. 18. By using high frequency pulse width modulation (PWM) of switch S, power may be supplied to solenoid 694 in accordance with desired profiles. An example of one such power profile 802 for powering a single actuation of the solenoid of a solenoid pump, such as solenoid 694 of pump 624, according to one particular, non-limiting embodiment of the present invention is shown in FIG. 22.

Figure 22:
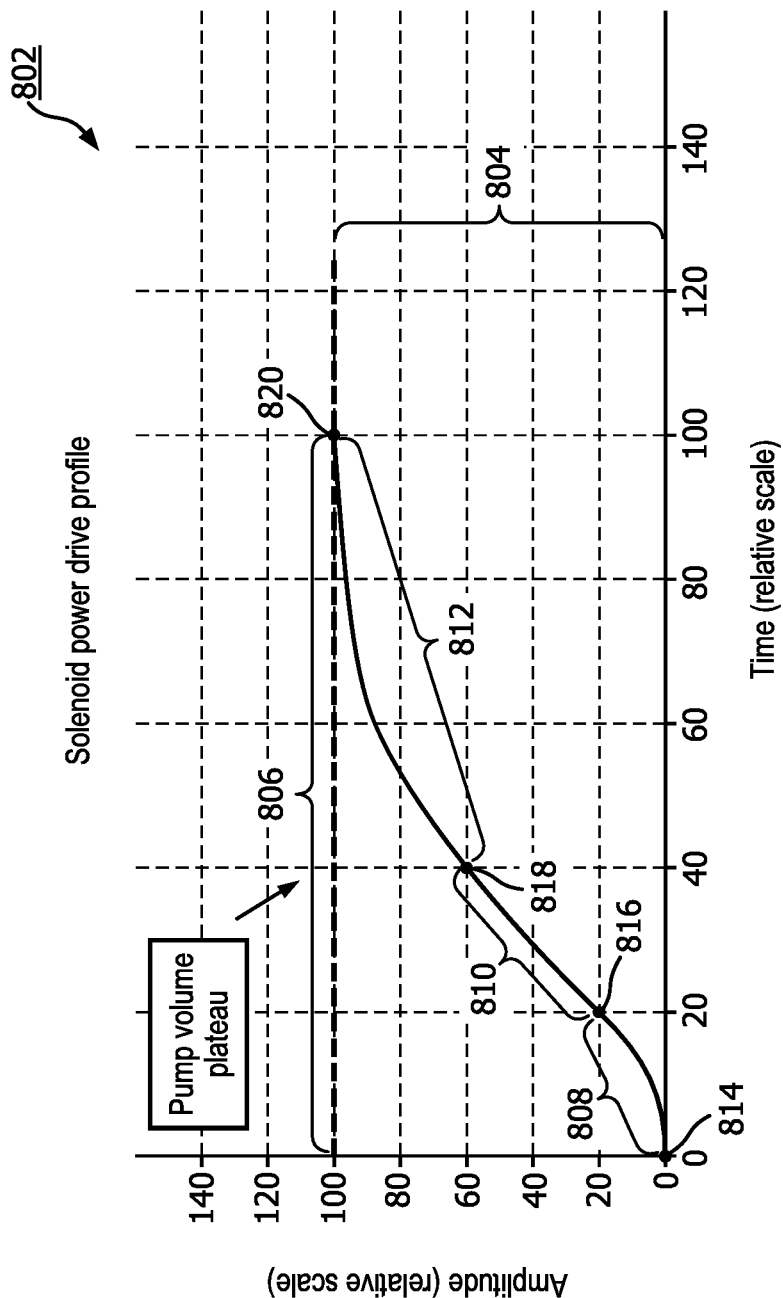
FIG. 22 is an example power delivery profile for operating a solenoid pump according to one particular, non-limiting embodiment of the present invention.

Power profile 802 extends between a pump volume range 804, which corresponds to movement of armature 696 from a starting to a fully extended position, and a total extension time 806, which in the example shown in FIG. 22 is expressed in a relative manner (i.e., the time for a full extension takes 100% of an extension time). In order to provide quiet operation of solenoid power profile generally includes: an initial portion 808 which increases generally at a first overall rate; an intermediate portion 810 which increases generally at a second overall rate greater than the first overall rate, and a final portion 812 which decreases at a third overall rate. Initial portion 808 extends from an initial (retracted) positioning 814 (i.e., 0,0) of armature 696 to a second positioning 816 which is about 20% of both range 804 and time 806 (i.e., about 20,20). Initial portion 808 generally increases at a slow rate near initial positioning 814 which then increases near second positioning 816. Intermediate portion 810 extends generally from second positioning 816 to third positioning 818 (i.e., about 40,60) which is about 40% of range 804 and 20% of time 806. Intermediate portion 810 generally increases initially at a greater rate closer to second positioning 816 and then at a generally slightly slower rate closer to third positioning 818. Final portion 812 extends generally from third positioning 818 to a final, generally fully extended, positioning 820 (i.e., about 100,100) which is about 40% of range 804 and 60% of time. Final portion 812 generally decreases at generally a first rate near third positioning 818 and then at a decreasing rate nearing final positioning 820. In an example embodiment of the present invention, power is further provided to solenoid 694 according to a mirror image (mirrored about a vertical axis passing through 100,100) of power profile 802 during retraction of armature 696 in order to selectively counteract the forces applied by spring 696 in returning armature 696 back to initial positioning 0,0 in a controlled manner. By using such predetermined power profile(s), solenoid 696 is operated in a quiet manner which reduces/eliminates potential disturbances to a user of system 602.

A solenoid driven pump, such as pump 624 of FIG. 20, may require a nominal level of power to actuate the pump diaphragm 628 and valves 690 and 692, and have sufficient power to overcome static forces to move the fluid through the pump. But such a system may require a startup routine in which a greater power level than the nominal level is needed to overcome initial static conditions. If a fluid pump remains idle for an extended period of time the one-way flow valves such as 690 and 692 may begin to stick in which nominal pumping power is insufficient to overcome. A method to overcome this initial stuck condition is to modulate the pump driving energy at or near (+/−about 5%) a resonant frequency of the pump system during the startup phase. Driving the pump at the resonant frequency provides a maximum force to the active one-way valve, as well as increased power to the passive one-way valve. In an example embodiment in which the power supply to the solenoid actuator is implemented with an H-bridge style power driver, then the polarity of the power to the solenoid can be alternated between forward and reverse polarity at the resonant frequency. This method results in delivering equal power to unstick both one-way valves.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pump arrangement for powering a pump in providing a controlled volume of water to a drip nozzle in a drip-feed humidifier, the pump arrangement comprising:
    a pump having a solenoid, an armature, a diaphragm member, and a spring, wherein the diaphragm member forms a portion of a pumping chamber and is deformable between an initial position for a given volume of the pumping chamber and a deformed position which reduces the given volume of the pumping chamber, wherein the armature is coupled to the diaphragm member to deform the diaphragm member away from the solenoid and the initial position in response to the solenoid being energized, and wherein the spring is tensioned to pull the armature back toward the solenoid and move the diaphragm member back to the initial position;
    a processing unit; and
    a power supply electrically connected to the solenoid via a switch (S) which is controlled by the processing unit, the power supply is structured to supply power to energize the solenoid via the switch,
    wherein the processing unit is configured to pulse width modulate the power provided to the solenoid via the switch, wherein pulse width modulating the power comprises energizing the solenoid according to a power drive profile for each actuation of the solenoid for extending the armature from a starting position to a fully extended position in a quiet manner which is below a given noise threshold of potential disturbance, and
    wherein the power drive profile, defined via a pump volume having a relative scale from zero to 100 percent, corresponding to an overall pump volume range determined via movement of armature positioning from the starting position to the fully extended position, versus an extension time having a relative scale from zero to 100 percent, corresponding to an overall extension time range for movement of the armature positioning from the starting position to the fully extended position, comprises:
        an initial portion of the power drive profile for providing initial power delivery that increases at a first overall rate and energizing the solenoid to cause an initial movement of the armature in a direction from the starting position to a second position, wherein the initial portion extends over a predetermined initial percentage of both the overall pump volume range and the overall extension time of the power drive profile from the starting position of the armature to the second position of the armature,
        an intermediate portion of the power drive profile for providing intermediate power delivery that increases at a second overall rate different than the first overall rate and energizing the solenoid, subsequent to the initial portion, to cause an intermediate movement of the armature in the direction from the second position to a third position, and
        a final portion of the power drive profile for providing final power delivery which decreases at a third overall rate different than either of the second or first overall rate and energizing the solenoid, subsequent to the intermediate portion, to cause a final movement of the armature in the direction from the third position to the fully extended position, wherein each corresponding energization of the solenoid is operated in the quiet manner.

2. The pump arrangement of claim 1, wherein the second overall rate is greater than the first overall rate.

3. The pump arrangement of claim 2, wherein the second overall rate is twice the first overall rate.

4. The pump arrangement of claim 1, wherein the initial portion extends over the predetermined initial percentage that comprises 20% of both the overall pump volume range and the overall extension time of the power drive profile from the starting position of the armature to the second position of the armature.

5. The pump arrangement of claim 4, wherein the initial portion increases at a slow rate near the starting position which then increases near the second position, corresponding with the initial movement of the armature in the direction from the starting position to the second position.

6. The pump arrangement of claim 4, wherein the intermediate portion extends over an intermediate 40% of the overall pump volume range, subsequent to the initial 20% of the overall pump volume range, and over an intermediate 20% of the overall extension time, subsequent to the initial 20% of the overall extension time, from the second position to the third position.

7. The pump arrangement of claim 6, wherein the intermediate portion increases at a second rate closer to the second position and at a third rate, slower than the second rate, closer to the third position, corresponding with the intermediate movement of the armature in the direction from the second position to the third position.

8. The pump arrangement of claim 4, wherein the final portion extends over a final 40% of the overall pump volume range, subsequent to the intermediate 40% of the overall pump volume range, and over a final 60% of the overall extension time, subsequent to the intermediate 20% of the overall extension time, from the third position to the fully extended position.

9. The pump arrangement of claim 8, wherein the final portion decreases at a first rate near the third position and then at a decreasing rate nearing the fully extended position, corresponding with the final movement of the armature in the direction from the third position to the fully extended position.

10. The pump arrangement of claim 1, further wherein the spring is tensioned to pull the armature back toward the solenoid and move the diaphragm member back to the initial position in an absence of the solenoid being energized.

11. A pump arrangement for powering a pump in providing a controlled volume of water to a drip nozzle in a drip-feed humidifier, the pump arrangement comprising:
- a pump having a solenoid, an armature, a diaphragm member, and a spring, wherein the diaphragm member forms a portion of a pumping chamber and is deformable between an initial position for a first volume of the pumping chamber and a deformed position for a second volume of the pumping chamber different from the first volume, wherein the armature is coupled to the diaphragm member, and wherein the spring is tensioned to move the diaphragm member back to the initial position from the deformed position;
- a processing unit; and
- a power supply electrically connected to the solenoid via a switch (S) which is controlled by the processing unit, the power supply is structured to supply power to energize the solenoid via the switch,
- wherein the processing unit is configured to pulse width modulate the power provided to the solenoid via the switch, wherein pulse width modulating the power comprises energizing the solenoid according to a power drive profile for each actuation of the solenoid for extending the armature from a starting position to a fully extended position in a quiet manner which is below a given noise threshold of potential disturbance, and
- wherein the power drive profile, defined via a pump volume having a relative scale from zero to 100 percent, corresponding to an overall pump volume range determined via movement of armature positioning from the starting position to the fully extended position, versus an extension time having a relative scale from zero to 100 percent, corresponding to an overall extension time range for movement of the armature positioning from the starting position to the fully extended position, comprises:
  - an initial portion of the power drive profile for providing initial power delivery that increases at a first overall rate and energizing the solenoid to cause an initial movement of the armature in a direction from the starting position to a second position intermediate the starting position and the fully extended position, wherein the initial portion extends over a predetermined initial percentage of both the overall pump volume range and the overall extension time of the power drive profile from the starting position of the armature to the second position of the armature,
  - an intermediate portion of the power drive profile for providing intermediate power delivery that increases at a second overall rate different than the first overall rate and energizing the solenoid, subsequent to the initial portion, to cause an intermediate movement of the armature in the direction from the second position to a third position intermediate the second position and the fully extended position, and
  - a final portion of the power drive profile for providing final power delivery that decreases at a third overall rate different than either of the second or first overall rate and energizing the solenoid, subsequent to the intermediate portion, to cause a final movement of the armature in the direction from the third position to the fully extended position, wherein each corresponding energization of the solenoid is operated in the quiet manner.

12. The pump arrangement of claim 11, wherein the initial portion extends over the predetermined initial percentage that comprises 20% of both the overall pump volume range and the overall extension time of the power drive profile from the starting position of the armature to the second position of the armature.

13. The pump arrangement of claim 12, wherein the initial portion increases at a slow rate near the starting position which then increases near the second position, corresponding with the initial movement of the armature in the direction from the starting position to the second position.

14. The pump arrangement of claim 12, wherein the intermediate portion extends over an intermediate 40% of the overall pump volume range, subsequent to the initial 20% of the overall pump volume range, and over an intermediate 20% of the overall extension time, subsequent to the initial 20% of the overall extension time, from the second position to a third position.

15. The pump arrangement of claim 14, wherein the intermediate portion increases at a second rate closer to the second position and at a third rate, slower than the second rate, closer to the third position, corresponding with the intermediate movement of the armature in the direction from the second position to the third position.

16. The pump arrangement of claim 12, wherein the final portion extends over a final 40% of the overall pump volume range, subsequent to the intermediate 40% of the overall pump volume range, and over a final 60% of the overall extension time, subsequent to the intermediate 20% of the overall extension time, from the third position to the fully extended position.

17. The pump arrangement of claim 16, wherein the final portion decreases at a first rate near the third position and then at a decreasing rate nearing the fully extended position, corresponding with the final movement of the armature in the direction from the third position to the fully extended position.

* * * * *